United States Patent [19]

Samson et al.

[11] Patent Number: 4,988,799
[45] Date of Patent: Jan. 29, 1991

[54] LIGNOSULFONATE BASED PHARMACOLOGIC AGENT WITH ANTI-COAGULANT AND ANTI-THROMBOTIC ACTIVITY

[75] Inventors: Russell H. Samson, Sarasota, Fla.; John W. Hollis, Jr., Schofield, Wis.

[73] Assignee: Daishowa Chemicals Inc., Rothschild, Wis.

[21] Appl. No.: 84,620

[22] Filed: Aug. 11, 1987

[51] Int. Cl.$^5$ .......................... C07G 1/00; A61K 31/70
[52] U.S. Cl. ...................................... 530/505; 162/16; 424/195.1; 514/22
[58] Field of Search ....................... 424/195.1; 514/22; 530/505; 162/16

[56] References Cited

U.S. PATENT DOCUMENTS

| | | | |
|---|---|---|---|
| Re. 24,213 | 9/1956 | Van Blaricom et al. | 530/505 |
| 2,710,254 | 6/1955 | Van Blaricom et al. | 530/505 |
| 3,297,676 | 1/1967 | Brauns | 530/505 |
| 4,562,236 | 12/1985 | Lin | 530/505 |
| 4,748,235 | 5/1988 | Dilling et al. | 530/505 |

FOREIGN PATENT DOCUMENTS 2055292 2/1972 Fed. Rep. of Germany.

OTHER PUBLICATIONS

Loomis et al., "Heparin-like Anticoagulant Action of Sulfonated Lignins from Commercial Waste Sulfite Liquor", Journal of Pharmacology and Experimental Therapeutics, vol. 109, pp. 21–25, 1953.

*Primary Examiner*—William R. Dixon, Jr.
*Assistant Examiner*—Anthony J. Green
*Attorney, Agent, or Firm*—Andrus, Sceales, Starke & Sawall

[57] ABSTRACT

A lignosulfonate useful pharmacologically as an antithrombotic that inhibits deep venous thrombophlebitis without effecting blood coagulation, and which causes no apparent increased bleeding or side effects. The lignosulfonate is isolated from softwood spent sulfite liquor, and is administered in low dosages of from about 0.05 to about 1.0 mg/milliter of blood. A method of making and administering the lignosulfonate is also disclosed.

16 Claims, No Drawings

LIGNOSULFONATE BASED PHARMACOLOGIC AGENT WITH ANTI-COAGULANT AND ANTI-THROMBOTIC ACTIVITY

BACKGROUND OF THE INVENTION

The present invention relates to pharmacologic agents, and more particularly to a lignosulfonate based pharmacologic agent having anti-coagulant and anti-thrombotic activity.

Thrombophlebitis, which involves blood clotting in the deep veins of the leg, remains one of the major post-operative surgical complications. Thrombophlebitis accounts for approximately one death in every 100 major operations and is also responsible for the death of many debilitated patients, patients in hospitals for periods of prolonged bed rest, and patients who have fractured hips or neurosurgical conditions. Thrombophlebitis is also a major complication of pregnancy and oral contraceptives. The danger of thrombophlebitis is that the thrombus or blood clot may result in morbidity of the leg or more importantly the clot may migrate to the lung resulting in a pulmonary embolism and subsequent death by blocking lung blood flow and oxygen exchange in the lung.

At present, patients in whom a phlebitis develops are given anti-coagulation therapy to prevent clot growth as well as new clot formation. The problem with an anti-coagulant is that it frequently results in undesirable excess bleeding in the patient. An anti-coagulant is typically used, however, because there is at present no known anti-thrombotic agent i.e. blood clot formation preventor, which isn't also an anti-coagulant.

The anti-coagulant heparin is currently widely utilized as a clot formation preventor, and is administered only by injection. Heparin is degraded in the gastrointestinal tract and must be replenished intravenously or via subcutaneous injection. Fortunately, if excess bleeding in a patient occurs with heparin, an intravenous antidote, namely protamine, may be administered to stop the action of heparin.

There are also orally administered anti-coagulants such as Coumadin and Warfarin. However, oral anti-coagulants take approximately 72 hours to build to a desired performance level, and the antidote, Vitamin K and plasma transfusion, which can reverse the anticoagulancy effect, take many hours to work.

A drug available from the Sandoz Company, under the trademark Embolex has recently become available and is a blend of heparin and dihydroergotamine or DHE. Embolex causes veno-constriction which decreases venous pooling and therefore stasis and risks of stasis and thrombosis. There are potential side effects such as gangrene because the product can also cause arterial spasms and its heparin component can cause bleeding.

Recently, some additional drugs have become available which help dissolve blood clots such as streptokinase, urokinase and tissue plasminogen activator. These compounds can also result in bleeding. Furthermore these drugs have not been used to prevent phlebitis.

In a study entitled "Heparin-Like Anti-coagulant Action of Sulfonated Lignins From Commercial Waste Sulfite Liquor", by T. A. Loomis and R. E. Beyer, published in The Journal of Pharmacology and Experimental Therapeutics, Vol. 109, pages 21-25, 1953, the anti-coagulant effect of sodium lignin sulfonate was demonstrated in mongrel dogs. However, acute toxicity was observed in that the dogs experienced behavioral changes as well as increased salivation and instability. Accordingly, Loomis and Beyer concluded that although an anti-coagulant effect could be achieved using sulfonated lignin fractions, the acute toxicity observed made the sulfonated lignin fractions unsatisfactory for use as a substitute for heparin in clinical anti-coagulant therapy thus limiting their value.

Additionally, Loomis and Beyer's study did not evaluate, or even consider, the antithrombotic without anticoagulancy aspect of sodium lignin sulfonate. Furthermore, it has been found that compounds prepared by methodology similar to that utilized by Loomis and Beyer demonstrate adverse effects on blood components, e.g. platelet aggregation, which would render such compounds unsatisfactory for use as antithrombotic agents or anticoagulants.

SUMMARY OF THE INVENTION

A lignosulfonate useful pharmacologically as an antithrombotic without affecting blood coagulation, and which causes no apparent increased bleeding or side effects. The lignosulfonate is isolated by an amine extraction process from softwood spent sulfite liquor, and is administered in low dosages of about 0.05 mg/milliter of blood to about 1.0 mg/milliter of blood. Preferably, these low dosages comprise an amount of about 0.1 to about 0.5 mg/milliter of blood. Advantageously, the present invention does not exhibit adverse effects on numerous blood components or blood reaction mechanisms.

In another aspect of the invention, a method of making the lignosulfonate comprises the steps of reacting an aqueous mixture of a lignosulfonate in an acid environment with a tertiary amine to form an amine lignosulfonate, separating the water insoluable amine lignosulfonate from the remainder of the mixture, reacting a solution of the amine-lignosulfonate in an alkaline environment with an alkali to form an M-lignosulfonate where M is selected from sodium, lithium, calcium, potassium, magnesium or ammonium and separating the M-lignosulfonate from the remainder of the solution. The M-lignosulfonate may then be dried and ground to a desired solid particulate form. Optionally, the M-lignosulfonate may be further purified such as by steam stripping and flash evaporation to remove substantially all traces of the amine. Additionally, the alkaline pH of the M-lignosulfonate may be reduced to a substantially neutral pH subsequent to the separation of the M-lignosulfonate from the solution so as to be more compatible with blood pH. However, this latter step must be performed without forming any new soluble impurities, and thus is preferably performed by treating the M-lignosulfonate with a sulfonated polystyrene resin, H+ cycle, which can be readily removed thereafter by filtration as M-polystyrene sulfonate.

In another aspect of the invention a method of making the antithrombotic lignosulfonate comprises the steps of extracting spent sulfite liquor in an acidic environment with a substantially water insoluble tertiary amine carried in a substantially water insoluble liquid, such as a higher alcohol, to form a substantially water insoluble amine lignosulfonate in alcohol phase and an aqueous phase largely free of lignosulfonate, separating the two phases, extracting the substantially water insoluble amine lignosulfonate in alcohol mix with an aqueous alkaline solution to form an aqueous M-lignosulfonate phase, where M is the cation Na+, Ca++, NH4+, K+, Li+, Mg++ or mixes thereof and a substantially lignosulfonate free, substantially water insoluble tertiary amine in alcohol phase. The alkaline aqueous M-lignosulfonate solution may be further purified by steam stripping and evaporation to remove traces of amine and alcohol. Additionally, the pH of the solution may be reduced to nearer neutral pH to precipitate impurities and render the solution pH compatible with blood pH. It is desirable for this step to be performed without adding soluble impurities to the system and thus it is preferably performed by treating the M-lignosulfonate solution with a water insoluble cation exchange resin such as a sulfonated polystyrene in the H+ cycle which can readily be removed in the M cycle along with other insolubles by filtration.

The substantially pure lignosulfonate may be prepared with a carrier such as water or blood plasma or a buffer solution to form a pharmaceutical preparation for injection into patients at low dosages in an amount effective to inhibit thrombus formation in blood without affecting blood coagulation.

DESCRIPTION OF THE PREFERRED EMBODIMENT

The lignosulfonate of the present invention is isolated from spent sulfite liquor and may be useful pharmacologically as an antithrombotic and anti-coagulant agent. The lignosulfonate compound inhibits thrombosis at low dosages without affecting blood coagulating factors such as PT, PTT or platelets and without causing any apparent increased bleeding or side effects. The lignosulfonate is preferably administered at dosages of about 0.05 to about 1.0 mg/milliter of blood, and preferably about 0.1 to about 0.5 mg/milliter of blood.

Lignosulfonates exist in large amounts in waste or spent sulfite liquor. Spent sulfite liquor is that portion of the wood solubilized in the acid sulfite pulping of plant materials, preferably hardwoods and/or softwoods. The plant material is cooked at elevated temperatures at a pH of less than pH 7 in a solution of $MHSO_3$ where M is the cation which can include $NH_4^+$, $Na^+$, $Ca^{++}$, $Mg^{++}$, $Li^+$ and $K^+$. Spent sulfite liquors are comprised mainly of M-lignosulfonates, about 40% to about 70%; reducing sugars, about 5% to about 30%, and oligosaccharides from about 2% to about 20%.

The well known process is commonly used in making cellulose pulp for the manufacture of paper products and/or rayon. Most of the cellulose is not dissolved in the pulping process. The solubilized portion of the wood, i.e. the spent sulfite liquor, contains a substantial portion of the starting wood, 20 to 70% and usually 40 to 60%. Because of pulp washing, the spent sulfite liquor solids may range from about 5% to about 20%. Such a solution can be used in the present invention as well as concentrated solutions at about 40% solids to about 65% solids or dried spent sulfite liquor at about 90% to about 100% solids.

As used herein, the term "Kraft lignin" has its normal connotation, and refers to the substance which is typically recovered from alkaline pulping black liquors, such as are produced in the Kraft, soda and other well known alkaline pulping operations. The term "sulfonated lignin", as used in the specification, refers to the product which is obtained by the introduction of sulfonic acid groups into the Kraft lignin molecule, as may be accomplished by reaction of the Kraft lignin with sulfite or bisulfite compounds, so that Kraft lignin is rendered soluble in water. As used herein, the term "sulfite lignin" refers to the reaction product of lignin which is inherently obtained during the sulfite pulping of wood, and is a principle constituent of spent sulfite liquor. The term "lignosulfonate" ($LSO_3$) encompasses not only the sulfite lignin, but also the sulfonated lignin herein above described. Any type of lignosulfonate i.e., crude or pure may initially be employed so long as the lignosulfonate is obtained from softwood. For example, calcium lignosulfonates, sodium lignosulfonates, ammonium lignosulfonates, magnesium lignosulfonates, potassium lignosulfonates, lithium lignosulfonates, modified lignosulfonates, and mixtures or blends thereof may all be initially utilized herein. Lignosulfonates are available from numerous sources, in either aqueous solution or dried powder forms. For example, Reed Lignin, Inc. sells lignosulfonates under the trade designation "Lignosol" and "Norlig" which are appropriate for use in the present invention.

Exemplary of the efficacy and advantages of the present invention are the following examples, wherein all parts and percentages are on a weight basis, unless specified otherwise.

EXAMPLE I

This Example illustrates the process for making the lignosulfonate of the present invention.

Softwood spent sulfite liquor (SSL) is evaporated to 50–55% total solids removing essentially all free $SO_2$ to less than 0.2%. The SSL is diluted to about 40% solids, heated to 60° C. and maintained at that temperature with good agitation. The pH is adjusted to pH 2.5–3.0 using 10N sulfuric acid while simultaneously adding a 17–20% solution of dimethylhexadecyl amine in isooctanol so that total amount of dimethylhexadecyl amine added is 60–70% molarly equivalent to SSL sulfonic sulfur content. Agitation is continued for 15 minutes at 60° C. after all amine has been added. The entire mix is then dropped into a separatory vessel in which there is a phase separation. Lignosulfonate-amine is retained in the upper phase and some lignosulfonate, oligosaccharides and free sugars remain in the lower aqueous phase. When separation is complete, the aqueous lower phase is withdrawn and discarded. The lignosulfonate-amine in alcohol is transferred to a separate container. One volume is treated with about 0.5 volumes of distilled water while agitating. The mix is heated to about 60° C. and the pH is adjusted to about pH 9.5 with 50% sodium hydroxide. This mix is then transferred to a separatory vessel and two phases are allowed to form. The lower phase, containing sodium lignosulfonate in aqueous solution, is separated from the nearly lignosulfonate-free dimethylhexadecyl amine in isooctanol top fraction for further processing.

The sodium lignosulfonate fraction is stripped with live steam to remove traces of amine and alcohol. Following steam stripping, the material is additionally diluted and becomes cloudy. It is evaporated in a flash concentrator in vacuo with intermittent water addition.

Following evaporation, the pH is adjusted from pH 9.5 to pH 7.1 with Amberlite IRA-120 which is sulfonated polystyrene resin available from the Rohm and Haas Company. The Amberlite IRA-120 and other formed insolubles are removed by filtration over Whatman 42 paper. The resulting solution is tray dried 96 hours at 60° C. in a forced air oven. The product is removed from the tray and ground to desirable particle size.

Although Example I specifies sodium hydroxide, any alkali may be utilized including hydroxides and carbonates of $NH_4^+$, $Na^+$, $K^+$, $Li^+$, $Ca^{++}$ and $Mg^{++}$. Preferably, the alkaline environment is provided by any hydroxyl ion ($OH^-$) containing alkali, preferably a caustic alkali such as lithium, ammonium, potassium, calcium or sodium hydroxide. Additionally, amines other than dimethylhexacecyl amine may be utilized in the preparation of the lignosulfonate. For example, diethylhexadecyl, ethymethylhexadecyl, and dimethylheptadecyl amines, may also be utilized. Likewise, alcohols such as n-octyl, isoamyl, and hexyl and amyl may be used in addition to isooctanol, and broadly other water immiscible solvents for amines so that phase separation processes may be conveniently used during the separation steps required in Example I.

EXAMPLE 2

This Example illustrates the preparation of lignosulfonate compounds utilizing a methodology similar to the procedure utilized by the prior art method disclosed in the study entitled "Heparin-Like Anti-Coagulant Action Of Sulfonated Lignins From Commercial Waste Sulfite Liquor" by T. A. Loomis and R. E. Beyer, published in the Journal of Pharmacology and Experimental Therapeutics, Vol. 109, pages 21-25, 1953. This Example 2 is presented to illustrate together with Table I herein that the preparation of a lignosulfonate compound in a manner similar to the prior art Loomis and Beyer reference does not produce a pharmacologic agent that inhibits thrombis formation without effecting blood coagulation.

Two and one half liters of dilute (12-15% solids) crude spent sulfite liquor stripped of sulfur dioxide by boiling were passed over a cation exchange resin (Amberlite IRA-120 $H^+$) cycle in a column thus converting the calcium base lignosulfonate to lignosulfonic acid. After washing the column with distilled water the resulting lignosulfonic acid solution volume is 3.5 liters and pH 1.5. The pH of the solution was adjusted to pH 5.1 with $Ba(OH)_2.8H_2O$ to form a barium lignosulfonate solution. This solution was sequentially filtered over medium porosity sintered glass, 5 μm and 1.2 μm cellulose acetate membranes en vacuo. The solution was concentrated to about 50% total solids en vacuo by a rotary evaporator at 75°-80° C. Three barium lignosulfonate fractions were obtained by sequential additions of 250 ml and after insolubles isolation by filtration over Whatman #42 filter paper subsequent treatment of filtrate with 300 ml of ethanol and insolubles isolation by filtration over Whatman #42 filter paper. The soluble filtrate is the third fraction and was discarded.

The two isolated fractions were redissolved in water, the first fraction redissolved being filtered over Whatman #42 paper and subsequently 1.2 μm cellulose acetate membrane to remove undissolved impurities. This first barium lignosulfonate fraction was concentrated and reprecipitated fractionally by sequential additions of 500 ml ethanol and Whatman #42 filtration followed by 1000 ml ethanol and Whatman #42 filtration. These two filtration residues are processed to give Compound 1 and Compound 2 (Table I). Redissolved fraction 2 was reprecipitated with 500 ml ethanol and isolated by Whatman #42 filtration and was processed to give Compound 3 (Table I).

The three isolates were dissolved in distilled water and separately passed over a cation exchange resin (Amberlite IRA 120 $H^+$ cycle) to remove barium and give lignosulfonic acid solutions. The solutions were adjusted to pH 7.0-7.2 using 5N sodium hydroxide giving a sodium lignosulfonate solution. Each solution was tray dried in a forced air oven at 60° C. for 48 hours. The three dried materials were ground by mortar and pestal to give Compound 1, Compound 2 and Compound 3 (Table I).

Twelve different forms of lignin compounds were produced for evaluation as a potential anti-coagulant and antithrombotic agent. Table 1 contains the analytical data for the twelve compounds prepared for evaluation. Compounds 1, 2, 3, 6, 7 and 8 were prepared similarly according to the Loomis and Beyer procedure described previously herein in Example 2. The first three compounds, namely compounds 1, 2 and 3 were prepared from softwood spent liquor (SSL), and the latter three compounds i.e. compounds 6, 7 and 8 were prepared from hardwood spent liquor (HSL). Compound 4 was prepared in accordance with the procedures set forth in Example 1 herein from softwood spent liquor (SSL), and compound 9 was also prepared in accordance with the procedure of Example 1 except from hardwood spent liquor (HSL). Compounds 5 and 10 represent the discard fractions from the dimethylhexadecyl amine extraction of compounds 4 and 9, respectively. Compounds 11 and 12 were prepared by isolating lignosulfonate from spent sulfite liquor with a weak base anion exchange resin, from softwood spent liquor (SSL) and hardwood spent liquor (HLS), respectively.

TABLE I

| | SOFTWOOD FRACTIONS | | | | | HARDWOOD FRACTIONS | |
|---|---|---|---|---|---|---|---|
| | (1) 0042-106-1 Ba Salt pp+ | (2) 0042-106-2 Ba Salt pp+ | (3) 0042-106-3 Ba Salt pp+ | (4) 0042-132 B-35 Lignin | (5) 0042-131-2 B-35 Sugar | (6) 0042-100-1 Ba Salt pp+ | (7) 0042-100-2 Ba Salt pp+ |
| % Solids | dry | dry | dry | dry | 30.28 | dry | dry |
| 3% pH | 5.8 | 5.4 | 5.5 | 6.7 | 3.3 | 5.9 | 5.9 |
| % $OCH_3$ | 10.14 | 10.93 | 9.94 | 11.19 | 0.4 | 8.99 | 10.25 |
| % Ca | 0.042 | 0.052 | 0.017 | 0.13 | 0.04 | 0.146 | 0.038 |
| % Na | 4.35 | 4.44 | 5.77 | 4.91 | 0.03 | 7.04 | 6.54 |
| % Ba | 0.54 | 0.34 | 0.44 | — | — | 0.027 | 0.027 |
| % N | 0.14 | 0.08 | 0.08 | 0.115 | 0.06 | 0.26 | 0.23 |
| % S | 5.20 | 5.87 | 6.11 | 6.35 | 0 | 5.73 | 5.83 |
| % NSS | 1.15 | 0.71 | 0.91 | 0.53 | 0 | 0.62 | 0.60 |
| % Sugars | 3.50 | 1.91 | 1.66 | 0.54 | 74.6 | 1.58 | 1.40 |
| UV: K solids | 10.82 | 10.79 | 10.52 | 11.53 | 0.08 | 7.94 | 8.14 |
| $KOCH_3$ | 106.71 | 98.72 | 105.83 | 103.04 | 21.0 | 88.32 | 79.41 |
| Phenolic OH | 1.57 | 1.68 | 1.70 | 2.06 | 0.001 | 1.14 | 1.37 |
| nm | 49.5 | 49.0 | 49.0 | 48.5 | 51.0 | 43.0 | 42.0 |
| $D^2$ | 1.49 | 1.59 | 1.62 | 1.58 | — | 0.98 | 0.98 |
| Mw | 97,848 | 28,449 | 21,530 | 48,606 | — | 31,153 | 15,439 |

TABLE I-continued

| | | | | | | | |
|---|---|---|---|---|---|---|---|
| Mn | 29,326 | 11,469 | 8,284 | 8,714 | — | 9,909 | 7,555 |
| Mw/Mn | 4.81 | 2.48 | 2.60 | 5.57 | — | 3.15 | 2.05 |
| % NaLSO$_3$ | 82.02 | 90.96 | 84.36 | 94.9 | — | 58.46 | 64.73 |
| % of SSL Solids | 15.4 | 20.3 | 9.6 | 23.88 | | 10.6 | 6.8 |
| Mean Clot Time (seconds) | 600* | 600* | 232 | 600** | 160 | 423 | 335 |

| | HARDWOOD FRACTIONS | | | ION EXCHANGED SAMPLES | | |
|---|---|---|---|---|---|---|
| | (8) 0042-100-3 Ba Salt pp+ | (9) 0020-33 Lignin | (10) 0042-131-1 B-35 Sugar | (11) 0044-38-1 Softwood | (12) 0045-38-2 Hardwood | BLOOD CONTROL |
| % Solids | dry | dry | 28.41 | dry | dry | |
| 3% pH | 5.5 | 7.98 | 2.6 | 9.3 | 7.1 | |
| % OCH$_3$ | 10.15 | 11.31 | 1.08 | 12.84 | 15.62 | |
| % Ca | 0.017 | 0.81 | 0.04 | 0.02 | 0.01 | |
| % Na | 6.69 | 5.57 | 0.004 | 6.79 | 5.34 | |
| % Ba | 0.014 | — | — | — | — | |
| % N | 0.19 | 0.21 | 0.023 | 0.06 | 0.14 | |
| % S | 5.87 | 7.13 | 0 | 5.12 | 4.85 | |
| % NSS | 0.62 | 0.73 | 0 | 0.26 | 0.20 | |
| % Sugars | 0.77 | 1.34 | 78.54 | 0.14 | 0.31 | |
| UV: K solids | 7.61 | 9.41 | 0.23 | 12.87 | 11.15 | |
| KOCH$_3$ | 74.98 | 83.16 | 20.93 | 100.23 | 71.38 | |
| Phenolic OH | 1.41 | 1.67 | 0.02 | 1.99 | 1.80 | |
| nm | 42.0 | 39.0 | 49.0 | 48.5 | 42.0 | |
| D$^2$ | 0.93 | 0.76 | — | 1.54 | 1.00 | |
| Mw | 7,252 | 23,773 | — | 50,651 | 43,503 | |
| Mn | 4,166 | 3,173 | — | 11,429 | 6,651 | |
| Mw/Mn | 1.74 | 7.49 | — | 4.42 | 6.53 | |
| % NaLSO$_3$ | 64.33 | 73.5 | — | 103.0 | 88.0 | |
| % of SSL Solids | 5.8 | 54.9 | | | | |
| Mean Clot Time (seconds) | 238 | 300 | 159 | 574*** | 463 | 126**** |

*Not clotted in 3 hrs.
**Range: 591–600
***Readings: 387, 493, 600
****Range: 78–217

The following summarizes the experimental evaluation of the twelve different compounds in Table 1 for their anti-coagulant and antithrombotic effects.

The 12 distinct lignin compounds were studied as to their effects on the mechanism of human blood coagulation and platelet aggregation in-vitro. At an added concentration of 1 mg/ml of lignin to 3.2% sodium citrate anti-coagulated plasma Compounds 1, 2, 3, 4, 6, 11 and 12 gave prolongation of prothrombin and partial thromboplastin times. The other five compounds did not and therefore were not considered further. Compounds 1, 2, 4 and 11 mildly reduced plasma fibrinogen. Protamine sulfate, which reverses the above effects from heparin did not neutralize the potency of Compounds 1, 2, 4 and 11. Compounds 1, 2 and 4 prolonged reptilase time suggesting interference in fibrinogen cleavage and fibrin monomer/polymer formation. Compound 11 did not and therefore was not considered further.

Compounds 1, 2, and 4 were then analyzed as to their effect on platelet aggregation. These studies were suggested by in-vivo pilot studies in dogs which showed a thrombocytopenia following lignin treatment. It was hypothesized that the acute thrombocytopenia may have been caused by in-vivo spontaneous platelet aggregation with subsequent clearing of these aggregates by the spleen. Compounds 1 and 2 produced fine aggregates without the addition of platelet aggregating agents into a platelet suspension being mixed in a platelet aggregometer. Compound 4, however, caused no spontaneous platelet aggregation and did not interfere with the normal aggregation induced by adenosine diphosphate, collagen, epinephrine, arachidonic acid, or ristocetin. Compound 4 was thus considered to be the ideal anticoagulant inasmuch as it prolonged the PT and APTT but did not affect platelets.

Further coagulation studies using Compound 4 showed that factors V, VII, VIII and IX were markedly reduced while prothrombin was not affected at all. This suggests an effect of the compound on both the intrinsic and extrinsic pathways of coagulation, most probably on the final common pathway above prothrombin. The data are most consistent with an anti-coagulant property directed against, among other molecules, the prothrombinase complex.

Additionally, the following Table II demonstrates that Compound 4, as compared to Compound 9, has no effect on platelet aggregation yet significantly increases clotting time as measured by ACT, PT and PTT.

TABLE II

| Compound 1 mg/ml | ACT** Seconds | PT* Seconds | PTT* Seconds | Platelet Aggregation |
|---|---|---|---|---|
| #4 | >600/126 | 29/11 | >180/31 | None |
| #9 | 300/126 | 11/11 | 28/31 | Aggregation | numerator = recorded value
denominator = control value
*In Vitro Human Blood
**Dog Blood in Vitro Compound 4 was then tested using in-vivo blood coagulation studies.

1. The ACT of greyhound dog blood was measured in-vivo after injection of 125 mg Compound 4 Kg dog body weight. Total anti-coagulation (i.e. ACT>600 seconds) occurred from within one minute of injection and persisted for at least three hours. The anticoagulant effect reversed by 24 hours. However, behavioral changes were noted in the animals in the first 15 minutes (i.e. increased salivation, unsteadiness and anxiety). These changes abated by 20 minutes. Furthermore, extensive bleeding occurred from the venipuncture sites. The platelet count fell significantly in all animals within five minutes of injection, but returned to normal levels by three hours.

2. The antithrombotic and anti-coagulant effects of low doses of Compound 4 were measured using a rabbit thrombosis model. In this model, thrombus formation was induced in the rabbit internal jugular vein by the following method. White New Zealand rabbits weighing 2 kg. were anesthetized by Ketamine anesthesia. Both internal jugular veins were exposed via a mid-line incision, and 000 silk ligature loosely placed around each internal jugular so as to potentially isolate a 1 cm segment of vein. 3 cc's of blood was taken from the left ear artery in order to later measure PT, PTT and platelets. A thrombogenic state was then created by injecting Simplastin, which is a thromboplastin available from General Diagnostics, in dosages of either 360 micrograms or 720 micrograms into the left rabbit ear vein. Fifteen seconds later the left internal jugular ligatures were tied in order to completely isolate a segment of vein and then, similarly, the right internal jugular vein segment was isolated. Immediately thereafter a further 3 cc's of blood was removed for later evaluation. Fifteen minutes later both isolated segments were removed and opened in order to assess the development of clot in the segments. Clot formation was graded as follows: 0=no clot; ½+ =serum clot only; 1+ =minimal visable clot involving all blood components; 2+ =moderate clot; 3+ =large amount of clot that did not completely fill the vein; 4+ complete occulsion of the isolated segment.

The antithrombotic effect of Compound 4 was studied using the same model with the following modifications. Having isolated the veins and withdrawing the control 3 cc's of blood, Compound 4 was injected into the right rabbit ear vein. When 720 micrograms of Simplastin were to be used, 15 mg of Compound 4 were injected. When 360 micrograms of Simplastin were to be used, 30 mg. of Compound 4 were injected. Five minutes after injection of the lignin, 3 cc's of blood were removed from the right ear artery for subsequent evaluation. Immediately thereafter the Simplastin was injected and the thrombosis model as outlined above continued.

No significant effect on the prothrombin time, APTT, thrombin time, reptilase time, fibrinogen level or platelet count was observed, as shown by the following data in Table III:

TABLE III

|  | Control (Sec.) | Lignin (Sec.) |
| --- | --- | --- |
| Prothrombin Time | 7.3 ± 1.0 | 7.0 ± 0.7 |
| APTT | 18.3 ± 1.2 | 19.3 ± 0.5 |
| Thrombin Time | 10.2 ± 1.1 | 10.4 ± 1.8 |

The above data demonstrates that Compound 4 has an insignificant effect on prothrombin time, APTT and thrombin time.

Despite the lack of anti-coagulant effect, a significant antithrombotic effect was demonstrated. Control animals had a mean thrombotic index of 2.3 while lignin Compound 4 animals had a score of 1.3.

In summary, Compound 4 significantly decreased the incidence of thrombus formation and also the amount of thrombus formed. This occurred despite any demonstrable effect on PT and PTT and with only a minimal effect on platelets. Compound 4 thus appears to have unique features that should allow it to be utilized pharmacologically as an antithrombotic and possible anticoagulant drug. In high dosages, Compound 4 causes significant changes in PT, PTT and platelet aggregation studies. Furthermore, bleeding time is also prolonged. In low dosages, none of these parameters were affected, yet significant prophylaxis of induced thrombosis was demonstrated.

Various modes of carrying out the invention are contemplated as being within the scope of the following claims particularly pointing out and distinctly claiming the subject matter which is regarded as the invention.

We claim:

1. A method of making a pharmacologic agent having anti-thrombotic activity, comprising the steps of:
   liquid-liquid extracting an aqueous mixture of a substantially sulfite-free spent sulfite liquor having a pH of 2 to 6 with an amine dissolved in a water immiscible alcohol to form an amine-lignosulfonate-alcohol liquid phase and an aqueous phase, wherein the amount of amine added to the sulfite liquor is 60–70% molarly equivalent to the original spent sulfite liquor sulfonic sulfur content;
   separating the amine-lignosulfonate-alcohol liquid phase from the aqueous phase;
   liquid-liquid extracting the amine-lignosulfonate-alcohol liquid phase with an alkali to form a M-lignosulfonate aqueous phase having a pH of 8 to 14, where M is selected from ammonium, sodium, potassium, lithium, calcium and magnesium, and a substantially lignosulfonate-free amine-alcohol liquid phase;
   separating the M-lignosulfonate aqueous phase from the amine-alcohol liquid phase;
   reducing the alkaline pH of the M-lignosulfonate aqueous phase to a substantially neutral pH while simultaneously forming insoluble impurities subsequent to the separation of the M-lignosulfonate and amine-alcohol liquid phases by treating the M-lignosulfonate aqueous phase with a cation exchange resin; and
   separating the insoluble impurities from the M-lignosulfonate.

2. The method of claim 1 wherein said alkali is selected from the group consisting of lithium, ammonium, potassium, calcium and sodium hydroxide.

3. The method of claim 1 wherein said alkali is selected from the group consisting of hydroxides and carbonates of ammonia, calcium and magnesium.

4. The method of claim 1 wherein said amine is diemthylhexadecyl amine.

5. The method of claim 1 further including the step of purifying the M-lignosulfonate aqueous phase to remove substantially all traces of the amine and the alcohol.

6. The method of claim 5 wherein said purifying step comprises stripping the M-lignosulfonate with steam.

7. The method of claim 6 further comprising the step of evaporating the M-lignosulfonate in a flash concentrator with intermittent water addition subsequent to the steam stripping of the M-lignosulfonate.

8. The method of claim 1 wherein said lignosulfonate is obtained from softwoods.

9. The method of claim 1 wherein said alcohol is isooctanol.

10. The method of claim 1 wherein said cation exchange resin is a sulfonated polystyrene resin.

11. A pharmaceutical composition comprising a lignosulfonate prepared by the process of claim 1 in an amount effective to inhibit thrombus formation in blood without effecting blood coagulation; and
   a pharmaceutically acceptable inert carrier for said lignosulfonate.

12. The pharmaceutical composition of claim 11 wherein said inert carrier is water.

13. The pharmaceutical composition of claim 11 wherein said inert carrier is blood plasma.

14. A method of administering a pharmaceutical composition, comprising the steps of:
   preparing a softwood lignosulfonate by liquid-liquid extracting an aqueous mixture of a substantially sulfite-free spent sulfite liquor having a pH of 2 to 6 with an amine dissolved in a water immiscible alcohol to form an amine-lignosulfonate-alcohol liquid phase and an aqueous phase, wherein the amount of amine added to the sulfite liquor is 60–70% molarly equivalent to the original spent sulfite liquor sulfonic sulfur content;
   separating the amine-lignosulfonate-alcohol liquid phase from the aqueous phase;
   liquid-liquid extracting the amine-lignosulfonate-alcohol liquid phase with an alkali to form a M-lignosulfonate aqueous phase having a pH of 8 to 14, where M is selected from ammonium, sodium, potassium, lithium, calcium and magnesium, and a substantially lignosulfonate-free amine-alcohol liquid phase;
   separating the M-lignosulfonate aqueous phase from the amine-alcohol liquid phase;
   reducing the alkaline pH of the M-lignosulfonate aqueous phase to a substantially neutral pH while simultaneously forming insoluble impurities subsequent to the separation of the M-lignosulfonate and amine-alcohol liquid phases by treating the M-lignosulfonate aqueous phase with a cation exchange resin;
   separating the insoluble impurities from the M-lignosulfonate;
   mixing said lignosulfonate with a pharmaceutically acceptable inert carrier; and
   administering said mixture to a patient at a low dosage in an amount effective to inhibit thrombus formation in blood without affecting blood coagulation.

15. The method of claim 14 wherein said low dosage comprises an amount of about 0.05 to about 1.0 mg/milliliter of blood.

16. The method of claim 14 wherein the M-lignosulfonate aqueous phase has a pH of 9.5 to 11.

* * * * *